(12) United States Patent
Ainsworth et al.

(10) Patent No.: US 11,352,663 B2
(45) Date of Patent: Jun. 7, 2022

(54) USE OF ANTICOAGULANTS IN THE POLYMERASE CHAIN REACTION

(71) Applicant: Genedrive Diagnostics Ltd, Manchester (GB)

(72) Inventors: Shaun Ainsworth, Manchester (GB); Ben Cobb, Manchester (GB); Gino Miele, Manchester (GB)

(73) Assignee: Genedrive Diagnostics Ltd, Manchester (GB)

( * ) Notice: Subject to any disclaimer, the term of this patent is extended or adjusted under 35 U.S.C. 154(b) by 297 days.

(21) Appl. No.: 16/495,799

(22) PCT Filed: Mar. 16, 2018

(86) PCT No.: PCT/GB2018/050683
§ 371 (c)(1),
(2) Date: Sep. 19, 2019

(87) PCT Pub. No.: WO2018/172749
PCT Pub. Date: Sep. 27, 2018

(65) Prior Publication Data
US 2020/0024645 A1   Jan. 23, 2020

(30) Foreign Application Priority Data
Mar. 20, 2017   (GB) ..................... 1704401

(51) Int. Cl.
C12P 19/34   (2006.01)
C12Q 1/686   (2018.01)
C12Q 1/6806  (2018.01)

(52) U.S. Cl.
CPC .......... *C12Q 1/686* (2013.01); *C12Q 1/6806* (2013.01); *C12Q 2527/125* (2013.01)

(58) Field of Classification Search
CPC ...................................... C12Q 1/686
See application file for complete search history.

(56) References Cited

U.S. PATENT DOCUMENTS

| | | | |
|---|---|---|---|
| 2002/0102660 A1* | 8/2002 | Nakayama | C12Q 1/686 435/91.2 |
| 2005/0277121 A1 | 12/2005 | Pasloske et al. | |
| 2009/0286251 A1* | 11/2009 | Xu | C12Q 1/6844 435/6.18 |
| 2011/0275073 A1* | 11/2011 | Gocke | C07K 14/4746 435/6.11 |
| 2011/0275126 A1* | 11/2011 | Kozuka | C12N 15/1003 435/91.2 |
| 2012/0258500 A1 | 10/2012 | Cheng | |
| 2013/0115601 A1* | 5/2013 | Bunce | C12Q 1/6881 435/6.11 |
| 2014/0234830 A1* | 8/2014 | Exner | C12Q 1/686 435/5 |

FOREIGN PATENT DOCUMENTS

| | | |
|---|---|---|
| CN | 102286473 A | 12/2011 |
| WO | WO-83/03831 A1 | 11/1983 |
| WO | WO-00/18965 A1 | 4/2000 |
| WO | WO-2012/038750 A1 | 3/2012 |
| WO | WO-2012/059751 A2 | 5/2012 |
| WO | WO-2012/093261 A1 | 7/2012 |
| WO | WO-2012/138417 A1 | 10/2012 |

OTHER PUBLICATIONS

Abbaszadegan, M. et al., Detection of enteroviruses in groundwater with the polymerase chain reaction. *Appl. Environ. Microbiol.* 59, 1318-1324 (1993).
Ahokas, H. and Erkkila, M., Interference of PCR amplification by the polyamines, spermine and spermidine, *PCR Methods Appl.*, 3:65-68 (1993).
Akane, A. et al., Identification of the Heme Compound Copurified with Deoxyribonucleic Acid (DNA) from Bloodstains, a Major Inhibitor of Polymerase Chain Reaction (PCR) Amplification, *J. Forensic Sci.*, 39:362-372 (1994).
Al-Soud, W. and Radstrom, P., Identification and characterization of immunoglobulin G in blood as a major inhibitor of diagnostic PCR, *J. Clin. Microbiol.*, 38:345-350 (2000).
Al-Soud, W. and Radstrom, P., Purification and characterization of PCR-inhibitory components in blood cells, *J. Clin. Microbiol.*, 39:485-493 (2001).
Albert, Matthew, Point-of-care tests to revolultionise the clinical management of patients infected by Hepatitis C Virus, PoC HCV Final Report, 17 pages (2016).
Arakawa, T. and Timasheff, S., Stabilization of protein structure by sugars, *Biochemistry (Mosc.)*, 21:6536-6544 (1982).
Ballou, G. et al., The Heat Coagulation of Human Serum Albumin, *J. Biol. Chem.*, 153:589-605 (1944).
Belec, L. et al., Myoglobin as a polymerase chain reaction (PCR) inhibitor: A limitation for PCR from skeletal muscle tissue avoided by the use of thermus thermophilus polymerase, *Muscle Nerve*, 21:1064-1067 (1998).
Bickley, J. et al., Polymerase chain reaction (PCR) detection of Listeria monocytogenes in diluted milk and reversal of PCR inhibition caused by calcium ions, *Lett. Appl. Microbiol.*, 22:153-158 (1996).
Bondos, S. and Bicknell, A., Detection and prevention of protein aggregation before, during, and after purification, *Anal. Biochem.*, 316:223-231 (2003).
Boye, J. et al., Thermal Denaturation and Coagulation of Proteins, British Library, pp. 25-56 (CRC Press, 1997).
Bu, Y. et al., Direct polymerase chain reaction (PCR) from human whole blood and filter-paper-dried blood by using a PCR buffer with a higher pH, Analytical Biochemistry, 375:370-372 (2008).
Burkardt, Hans-Joachin, Standardization and quality control of PCR analyses, *Clin. Chem. Lab. Med.*, 38:87-91 (2000).

(Continued)

*Primary Examiner* — Kenneth R Horlick
(74) *Attorney, Agent, or Firm* — Choate, Hall & Stewart LLP; Brenda Herschbach Jarrell; Michael L. Vetter (57) ABSTRACT

The invention provides a method and kit for preventing inhibition of a thermal cycling reaction by protein coagulation in a sample.

15 Claims, 6 Drawing Sheets

(56) References Cited

OTHER PUBLICATIONS

Chi, Eva Y., Excipients and their Effects on the Quality of Biologics, Center for Boimedical Engineering, 9 pages (2012).
Das, U. et al., Inhibition of protein aggregation: supramolecular assemblies of arginine hold the key, *PloS One* 2, e1176, 9 pages (2007).
Demeke, T. and Jenkins, R., Influence of DNA extraction methods, PCR inhibitors and quantification methods on real-time PCR assay of biotechnology-derived traits, *Anal. Bioanal. Chem.*, 396:1977-1990 (2010).
Edwin, F. et al., Stabilization of molten globule state of papain by urea, *Biochem. Biophys. Res. Commun.*, 290:1441-1446 (2002).
Fredricks, D. and Relman, D., Improved amplification of microbial DNA from blood cultures by removal of the PCR inhibitor sodium polyanetholesulfonate, *J. Clin. Microbiol.*, 36:2810-2816 (1998).
Friedland, L. et al., Development of a polymerase chain reaction assay to detect the presence of Streptococcus pneumoniae DNA, *Diagn. Microbiol. Infect. Dis.*, 20:187-193 (1994).
Garcia, M. et al., Anticoagulants interfere with PCR used to diagnose invasive aspergillosis, *J. Clin. Microbiol.*, 40:1567-1568 (2002).
Geng, T. and Mathies, R., Minimizing inhibition of PCR-STR typing using digital agarose droplet microfluidics, *Forensic Sci. Int. Genet.*, 14:203-209 (2015).
Goldenberger, D., et al., A simple "universal" DNA extraction procedure using SDS and proteinase K is compatible with direct PCR amplification, *PCR Methods Appl.*, 4:368-370 (1995).
Halford, William, P., The essential prerequisites for quantitative RT-PCR, *Nat. Biotechnol.*, 17:835 (1999).
Hamada, H. et al., Effect of additives on protein aggregation, *Curr. Pharm. Biotechnol.*, 10:400-407 (2009).
Holodniy, M. et al., Inhibition of human immunodeficiency virus gene amplification by heparin, *J. Clin. Microbiol.*, 29:676-679 (1991).
Huggins, C. and Jensen, E., Thermal coagulation of serum proteins; the effects of iodoacetate, iodoacetamide, and thiol compounds on coagulation, *J. Biol. Chem.*, 179:645-654 (1949).
Ijzerman, M. et al., A method to remove environmental inhibitors prior to the detection of waterborne enteric viruses by reverse transcription-polymerase chain reaction, *J. Virol. Methods*, 63:145-153 (1997).
Izraeli, S. et al., Detection of gene expression by PCR amplification of RNA derived from frozen heparinized whole blood, *Nucleic Acids Res.*, 19:6051 (1991).
John, Maliyakal E., An efficient method for isolation of RNA and DNA from plants containing polyphenolics, *Nucleic Acids Res.*, 20:2381 (1992).
Katcher, H. and Schwartz, I., A distinctive property of Tth DNA polymerase: enzymatic amplification in the presence of phenol, *BioTechniques*, 16:84-92 (1994).
Kerwin, B. et al., Effects of Tween 80 and sucrose on acute short-term stability and long-term storage at -20 degrees C of a recombinant hemoglobin, *J. Pharm. Sci.*, 87:1062-1068 (1998).
Kreilgaard, L. et al., Effect of Tween 20 on freeze-thawing- and agitation-induced aggregation of recombinant human factor XIII, *J. Pharm. Sci.*, 87:1597-1603 (1998).
Lange, C. and Rudolph, R., Suppression of protein aggregation by L-arginine, *Curr. Pharm. Biotechnol.*, 10:408-414 (2009).
Monteiro, L. et al., Complex polysaccharides as PCR inhibitors in feces: Helicobacter pylori model, *J. Clin. Microbiol.*, 35:995-998 (1997).
Narhi, L. et al., Classification of protein aggregates, *J. Pharm. Sci.*, 101:493-498 (2012).
Neagu, A. et al., Fluctuations and the Hofmeister effect, *Biophys. J.*, 81:1285-1294 (2001).
Ochman, H. et al., Inverse Polymerase Chain Reaction, *Nat. Biotechnol.*, 8:759-760 (1990).
Opel, K. et al., A study of PCR inhibition mechanisms using real time PCR, *J. Forensic Sci.*, 55:25-33 (2010).
Reddy, R. et al., L-Arginine increases the solubility of unfolded species of hen egg white lysozyme, *Protein Sci. Publ. Protein Soc.*, 14:929-935 (2005).
Rossen, L. et al., Inhibition of PCR by components of food samples, microbial diagnostic assays and DNA-extraction solutions, *Int. J. Food Microbiol.*, 17:37-45 (1992).
Saulnier, P. and Andremont, A., Detection of genes in feces by booster polymerase chain reaction, *J. Clin. Microbiol.*, 30:2080-2083 (1992).
Schrader, C. et al., PCR inhibitors—occurrence, properties and removal, *J. Appl. Microbiol.*, 113:1014-1026 (2012).
Troutt, A. et al., Ligation-anchored PCR: a simple amplification technique with single-sided specificity, *Proc. Natl. Acad. Sci. USA*, 89:9823-9825 (1992).
Vincent, M. et al., Helicase-dependent isothermal DNA amplification, *EMBO Rep.*, 5:795-800 (2004).
Wei, T., et al., Novel approaches to mitigate primer interaction and eliminate inhibitors in multiplex PCR, demonstrated using an assay for detection of three strawberry viruses, *J. Virol. Methods*, 151:132-139 (2008).
Widjojoatmodjo, M. et al., The magnetic immuno polymerase chain reaction assay for direct detection of Salmonellae in fecal samples, *J. Clin. Microbiol.*, 30:3195-3199 (1992).
Wiedbrauk, D. et al., Inhibition of PCR by aqueous and vitreous fluids, *J. Clin. Microbiol.*, 33:2643-2646 (1995).
Wilson, Ian G., Inhibition and facilitation of nucleic acid amplification, *Appl. Environ. Microbiol.*, 63:3741-3751 (1997).
Yeku, O. and Frohman, M. Rapid amplification of cDNA ends (RACE), *Methods Mol. Biol. Clifton NJ*, 703:107-122 (2011).
Zeldis, J. et al., Direct Method for Detecting Small Quantities of Hepatitis B Virus DNA in Serum and Plasma using the Polymerase Chain Reaction, Journal of Clinical Investigation, 84(5):1503-1508 (1989).
Zoueva, O. et al., Aggregation of influenza virus ribonucleocapsids at low pH, *Virus Res.*, 85:141-149 (2002).
Lyapina, L. et al., Anticoagulant effects of a complex of high molecular weight heparin and arginine, Bull Exp Biol Med., 147(3):328-30 (2009).

\* cited by examiner

USE OF ANTICOAGULANTS IN THE POLYMERASE CHAIN REACTION

FIELD OF THE INVENTION

The invention relates to the identification of a combination of reagents that prevent the thermal coagulation of proteins in a sample during heating. The use of these reagents allows the direct input of plasma or serum into a thermal cycling reaction without the aggregation of proteins.

BACKGROUND TO INVENTION

1.1. Introduction

In the clinic, rapid and specific diagnosis of an infection is fundamental to directing successful treatment. Thermal cycling reactions facilitate diagnosis by enabling the efficient analysis of the nucleic acid in a sample. The polymerase chain reaction (PCR), for example, is a thermal cycling reaction that is used to amplify nucleic acids. PCR uses a series of DNA melting, annealing, and polymerisation steps at different temperatures to greatly 'amplify' the amount of DNA in a sample, allowing detection of sequences that may otherwise be present in the sample at very low levels. Sequences may be detected by use of labelled probes or by determining thermal hybridisation. Other thermal cycling applications are also known.

Efficient PCR requires unhindered interaction between PCR reagents and the nucleic acid target. Burdensome sample processing is therefore often necessary to remove components of a sample that may hinder these interactions. During PCR, for example, it is necessary to heat the sample and PCR reagents to temperatures sufficient to cause denaturing of many proteins found in patient sample and aggregates of these denatured proteins can then inhibit the PCR. It is well documented, for example, that heating plasma or serum to temperatures greater than 60° C. induces the protein constituents to aggregate together and form a solid gelatinous mass that inhibits a thermal cycling reaction[1,2]. Additionally, it is often necessary, as part of a diagnostic assay, to release genetic molecules by protease digestion of cellular, viral or bacterial structures[3]. The necessary protease must then be heat-inactivated to prevent it from inhibiting the thermal cycling reaction. Consequently, it is often not possible to directly input a diagnostic sample into the PCR reaction without a number of prior processing steps. To eliminate the possibility of contaminating proteins, it is therefore conventional practise to purify the DNA/RNA from a plasma or serum sample for subjecting it to a diagnostic Nucleic Acid Test (NAT) comprising a thermal cycling reaction.

The use of thermal cycling reactions for rapid and specific diagnosis is therefore limited by the presence of proteins in a sample, which may coagulate the sample during necessary processing steps, or increase the risk of coagulation during the thermal cycling reaction itself. There are a number of additives and agents used to prevent protein aggregation and sample coagulation in other contexts. However, these have not been used in thermal cycling reactions, given that many anticoagulants and anti-aggregation agents are also known or suspected to be potent PCR inhibitors.

1.2. Anti-Aggregation and Coagulation Additives

Anti-aggregation additives are widely used to assist protein expression and refolding in heterologous systems and to prevent coagulation of protein rich sample[1], reviewed by Hamada et al.[4] and Chi et al[5]. Anti-aggregation additives include direct inhibitors of protein aggregation such as amino acids (e.g. arginine, proline, lysine, glycine)[6], polyamines (e.g. putrescine, spermidine and spermine), detergents (e.g. sodium dodecyl sulphate (SDS), Tween 87, Tween 20[8], Nonidel P-40[9]) and denaturing agents (e.g. guanidinium hydrochloride (GuHCl) and urea[10]). Anti-aggregation additives also include agents that increase the stability of the native protein confirmation, such as sugars (e.g. sucrose, glucose, lactose, mannitol, sorbitol)[11], poly-alcohols and ammonium sulphate[12].

The appropriate type and concentration of an anti-aggregation additive can be optimised for different protein species and for whether the additive is required to assist protein refolding or to prevent sample coagulation[13]. Many anti-aggregation additives have only been shown to be effective when they are present as co-solvents, i.e. when they make up a significant fraction of the total mass of a solution (concentrations in the submolar to molar range)[14].

1.3. PCR Inhibitors

Inhibitors of PCR are many and varied, and include both organic and inorganic, soluble and insoluble substances[15]. Examples of PCR inhibitors include calcium ions[16], bile salts[17,18], urea[19], NaOH[20], phenol[21], ethanol[17], polyamines (e.g. spermine and spermidine[22]), polysaccharides[23,24] detergents (e.g. SDS), humic acids[25], tannic acid[19], melanin and proteins including collagen, myoglobin[26], haemoglobin[27], lactoferrin[17], immunoglobin G (IgG)[28], proteinases and anti-coagulants including heparin[17,29,30], sodium polyanetholesulfonate (SPS)[31], EDTA and citrate[32,33].

PCR inhibition can occur by any of a wide variety of different mechanisms[15]. These include binding, degrading, sequestering, co-precipitating or otherwise modifying the chemical properties of the nucleic acid target[21,34-37], reducing the specificity of the PCR primers[34] degrading[20,38] or inhibiting the polymerase[37] and/or sequestering cofactors of the polymerase[15,16]. It is therefore difficult and non-obvious to predict whether a particular agent will cause PCR inhibition, at what concentration this inhibition may take effect, and by what mechanism inhibition is caused.

1.4. PCR Inhibition by Anti-Aggregation Agents

There is significant overlap between PCR inhibitors, anti-aggregation additives and anticoagulants. PCR inhibition by standard anti-coagulants is well-documented, and present a particular challenge to PCR preformed on clinical samples, given that anticoagulants are often necessary for their collection and preservation, and their inhibitor effects can occur at very low concentrations[29]. Other PCR inhibitors occur naturally in the environment or sample fluid[25,39] or are required for sample processing (e.g. proteases)[40]. Consequently, if an anti-aggregation additive or anticoagulant is used during sample preparation, or is likely to be otherwise present in the sample, it is deemed necessary to extract the nucleic acid from the sample before it may be used in PCR. Given this, and the likelihood of the presence of other potential inhibitors of PCR in a sample, it is standard practise to purify the nucleic acid template before mixing it with the PCR reagents. Furthermore, purification of the template may remove the need for anti-aggregation, given that contaminating proteins and/or protein aggregates will also be removed by purification. Therefore, given that anti-aggregation additives and anticoagulants are often rendered unnecessary by conventional PCR purification protocols, their use during PCR processing has been severely limited.

In situations where purification of the template is not otherwise required or desirable, the inhibitory effects of a PCR inhibitor may be mitigated by dilution of the sample[41]. However, given that many inhibitors of PCR are effective at very low doses[29], this can significantly reduce the sensitivity of an assay. 1-2% of the anti-aggregate SDS, for example, is required to prevent aggregation of denatured protein, whilst as little as 0.01% SDS is sufficient to inhibit PCR[3]. Consequently, dilution of the sample to the extent that the anti-aggregate additive no longer inhibits PCR, also abolishes its anti-aggregate effects. It is therefore deemed necessary to purify aggregate proteins from the sample prior to performing the thermal cycling reaction[3].

It is also possible to neutralise the inhibitory effects of some PCR inhibitors by the addition of BSA[15]. However, BSA is ineffective against the inhibitory effects of anti-aggregate agents such as SDS, calcium and sodium chloride[15].

In summary, it is known in the field that protein aggregates and coagulants inhibit PCR. Clinical samples often have a high protein content and mixing these samples directly with PCR regents therefore either carries the risk of coagulating the sample during thermal cycling, or necessitates significant dilution of the sample. Clinical samples are therefore purified to extract the nucleic acid before thermal cycling is performed. Furthermore, if an anti-aggregation agent or anticoagulant is present in the sample (either because it is present naturally, or has been added during sample processing), its inhibitory effects are mitigated by purification or significant dilution of the sample.

1.5. Arginine in PCR

The use of arginine in PCR has been previously shown. US 2012/0258500A1 uses arginine, and other additives, to improve the specificity of nucleic acid amplification and reduce polymerase inhibition. Similarly, WO 2012/138417 discloses the use of an agent, including arginine, spermidine and/or spermine, at concentrations between 1 and 100 mM. US 2005/0277121 also discloses the use of amino acids such as arginine or glycine, in order to lower the pH of the reaction mixture to reduce cellular nuclease activity that may disrupt RT-PCR or other enzymatic reactions. However, the use of arginine as an anti-coagulant has not been demonstrated in the prior art.

Summary of Invention

The present invention provides an improved method for performing a rapid and efficient thermal cycling reaction. In particular, the invention provides a method for performing a thermal cycling reaction that does not require purification or significant dilution of the sample, wherein significant dilution is that which severely reduces the detection limit of the assay. A dilution that severely reduces the detection limit is one that reduces the detection limit by more than 3, 5, 10, 15 or 20 times. A significant dilution may be, for example, dilution by a factor of 4, 5, 6, 7, 8, 9, 10 or more. The invention is based on the surprising discovery that certain anticoagulant formulations do not inhibit PCR at concentrations at which they are effective as an anticoagulant. The invention provides a method comprising directly mixing an anticoagulant with a sample and the regents necessary for preforming a thermal cycling reaction. The anticoagulant acts to prevent inhibition of the thermal cycling reaction by denatured proteins that may either be already present in the sample or that are produced by the thermal cycling process. The addition of the anticoagulant renders unnecessary the purification of the sample in order to remove proteins and protein aggregates. The anticoagulant may also be directly mixed with the sample to prevent protein aggregation during sample processing, for example during heat-inactivation of a proteinase, without the need for additional purification steps to remove the protein aggregates and/or the anticoagulant prior to mixing the sample with the PCR reagents. The invention also relates to a formulation of the anticoagulant.

In one embodiment, the present invention relates to a method of performing a thermal cycling reaction comprising:
  a) mixing a sample with i) an anticoagulant and ii) reagents necessary for performing a thermal cycling reaction in the sample in the presence of a template, and
  b) incubating the sample under thermal cycling conditions, wherein the anticoagulant protects the thermal cycling reaction from inhibition by denatured proteins in the sample. The invention also relates to the reagents and kits for use in this method.

In one embodiment, the present invention relates to the use of arginine as an anticoagulant in a thermal cycling reaction, wherein the arginine prevents coagulation of protein in the sample resulting from heating. Preferably, the thermal cycling reaction is PCR and preferably arginine is used at a concentration of 2-6 mg/ml, more preferably 5 mg/ml.

ABBREVIATIONS

BSA bovine serum albumin
CSF cerebrospinal fluid
DNA deoxyribose nucleic acid
EDTA ethylenediaminetetraacetic acid
GuHCl guanidinium hydrochloride
HCV hepatitis C virus
$MgCl_2$ magnesium chloride
NAT nucleic acid tests
PCR polymerase chain reaction
RT-PCR real-time PCR
SDS sodium dodecyl sulphate
IgG immunoglobin G

DETAILED DESCRIPTION

Brief Description of the Figures

FIG. 1. Arginine prevents thermal induced coagulation of plasma proteins
A: the skeletal formula of arginine. B: The effect of L-, D- and L/D-arginine on plasma coagulation.

FIG. 4. Optimisation of L-arginine Concentration

The effect of different concentrations of L-arginine (0.625-5 mg/ml) on the coagulation of plasma diluted 1:3.

FIG. 5. Final reagent mix testing on plasma and serum

The coagulation of plasma or serum (neat or diluted 1:2 or 1:3), with or without supplementation with the optimized anticoagulant reagents (5 mg/ml L-arg, 50 mM Tris, 5 mM $MgCl_2$).

Definitions

Anticoagulant
an agent that reduces or prevents coagulation of a sample, including but not restricted to agents suitable for preventing blood clots. See also Coagulation.

Figure 1A:
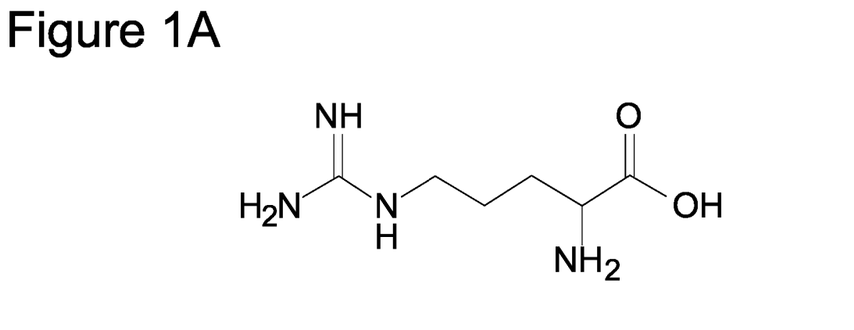

Arginine
amino acid having the chemical formula $CeH_{14}N_4O_2$ ($M_r$=174.20 g·mol$^{-1}$), also known as 2-Amino-5-guanidinopentanoic acid, Arg or R. FIG. 1A shows the skeletal formula of arginine. Arginine can exist in a L- or D-chimeric form.

Aggregation: See Protein Aggregation

Coagulation
change to a viscous or solid state caused by the change of a solute into an insoluble form or by the flocculation or separation of colloidal or suspended matter, for example the random aggregation of a denatured protein in solution into insoluble aggregates. See also Anticoagulant.

Denaturation
loss-of-function modification to the secondary, tertiary and/or quaternary structure of a protein that results in unfolding of the native protein structure[42]. See also Thermal Denaturation.

Flocculation
the process in which colloids come out of suspension in the form of flocs or flakes.

Target Nucleic Acid
the nucleic acid amplified or replicated by a thermal cycling reaction. In order for a thermal cycling reaction to occur the appropriate nucleic acid target must be present in a sample. The appropriate target will depend on the thermal cycling reaction and the sequences of the primers. The target nucleic acid may be present in for example, digested genomic DNA, viral DNA, ligated DNA, DNA copies of mRNA or viral genomic RNA or a DNA plasmid.

Thermal Cycling Reaction
a reaction comprising cycles of repeated heating and cooling facilitating nucleic acid melting and enzymatic replication. Thermal cycling reactions may also be referred to as temperature cycling reactions. PCR is an example of a thermal cycling reaction. There are a wide variety of thermal cycling reactions and types of PCR. The reagents necessary are well known in the field, and include a polymerase (e.g. Taq, Tma or Pfu), substrate for the polymerase (e.g. dNTPs) and the appropriate reaction and dilution buffers. Types of thermal cycling reaction include ligation mediated PCR (e.g. inverse PCR (IPCR)[43] and anchored PCR[44]), reverse transcriptase PCR (RT-PCR), quantitative RT-PCR[45], helicase dependent amplification (HAD)[46] and rapid amplification of cDNA ends (RACE)[47]. Depending on the type of reaction, thermal cycling regents may, for example, reverse transcriptase, DNA ligase, fluorescently labelled probes, helicase or DNase. See also Target nucleic acid.

Thermal Denaturation
protein unfolding caused by heat. See also Denaturation.

Protein Aggregation
a self-association reaction in which denatured proteins group together to form higher molecular weight complexes (aggregates)[48]. Protein aggregation is mediated by interaction between non-polar residues exposed during denaturation[49].

Description

The present invention relates to a method of performing a thermal cycling reaction comprising:
a. mixing a sample with i) an anticoagulant and ii) reagents necessary and sufficient for performing a thermal cycling reaction in the sample in the presence of a target nucleic acid, and
b. incubating the sample under thermal cycling conditions, wherein the anticoagulant protects the thermal cycling reaction from inhibition by proteins in the sample, particularly denatured proteins in the sample.

The thermal cycling reaction of the method is preferably PCR.

The Anticoagulant

In some embodiments the anticoagulant comprises arginine. In further embodiments, the sample is mixed with arginine to give a concentration of 2-6 mg/ml, preferably 5 mg/ml. In a still further embodiment the sample is diluted prior to the incubation step such that the concentration of arginine in the sample during the incubation step is 0.5-2 mg/ml, preferably 1.7 mg/ml. The arginine may be L-arginine, D-arginine or a mixture of D- and L-arginine. The anticoagulant may also be any suitable anti-aggregation agent that prevents inhibition of a thermal cycling reaction by denatured proteins that does not itself inhibit the PCR reaction in the absence of significant dilution of the sample or purification step.

The reagents necessary and sufficient for performing a thermal cycling reaction may also comprise the anticoagulant. In one embodiment, the anticoagulant and reagents may be provided in a single solution. The anticoagulant may comprise $MgCl_2$, preferably wherein the sample is mixed with $MgCl_2$ to give a $MgCl_2$ concentration of 2-6 mM, preferably 5 mM. The anticoagulant may comprises Tris, preferably Tris (pH 8.5), preferably wherein the sample is mixed with Tris to give a Tris concentration of 30-60 mM, preferably 50 mM.

The Protease and Heat Inactivation

In the method of the invention the sample may be supplemented with protease. In one embodiment the method of the invention comprises the additional step of mixing the sample with a protease, for example to release nucleic acid from cellular, viral or bacterial structures. The sample may be subjected to protein denaturing conditions, for example to heat inactivate the protease, prior to mixing with the anticoagulant and/or the reagents, preferably wherein subjecting the sample to denaturing conditions comprises heating the sample, preferably to 70-100° C., more preferably to 90-95° C., most preferably to 95° C. The sample is preferably heated for 1-20 minutes, preferably 5-10 minutes, most preferably for 5 minutes. Where heat inactivation of a protease is required, the denaturing conditions should be sufficient to deactivate the protease. The protease is preferably suitable for digesting a viral capsid, most preferably the Hepatitis capsid such as HCV, in order to release viral genetic material. The protease is preferably a serine protease isolated from a *Bacillus* strain.

Thermal Cycler

The method of the invention is suitable for being performed in a conventional thermal cycler. In one embodiment, the thermal cycling reaction is performed in a thermal cycler as described in WO 2012/038750[50], wherein the cycler comprises a sample block for receiving the sample, a Peltier-type thermoelectric element adjacent the sample block, configured for cooling the sample block, a non-Peltier-type heating device adjacent the sample block, configured for heating the sample block; a heat sink, separated from the sample block and Peltier-type element; and a heat pipe connecting the heat sink to the Peltier-type element, which permits thermal energy to transfer from the Peltier-type element to the heat sink. In some embodiments the sample block is sandwiched between the Peltier-type element and the non-Peltier-type heating device and/or further comprises an optics assembly.

The method of the invention may form part of a diagnostic test as described in WO/2012/093261[51], wherein the diagnostic test uses a reaction vessel having an identification tag (e.g. an RFID tag) readable by a remote reader; and a thermal cycler including a remote reader and means for reading a computer readable medium, the method comprising:
a) reading a readable tag from a reaction vessel, to determine the identity of the vessel;
b) comparing the identity of the vessel with data obtained from the computer readable medium representing one or more reaction vessel identities and associated processing steps of a diagnostic test;
c) selecting an appropriate processing step associated with the reaction vessel identity to perform;
d) performing the selected processing step on the reaction vessel; and
e) displaying the result of the performed processing step
wherein the sample for use in the diagnostic test is contained in the reaction vessel.

Sample

The sample used in the present invention may be derived from blood. The sample may comprise serum or plasma. In one embodiment that the sample comprises serum or plasma diluted in water, preferably to a ratio between 1:2 and 1:4, most preferably to a ratio of 1:3. The sample may also be derived from other body fluids or tissues, for example cerebrospinal fluid (CSF), amniotic fluid, bile, mucus, saliva, semen, aqueous humour, lymph, synovial fluid faeces. The sample may be derived from a biopsy.

The sample may be processed or stored prior to use, for example frozen or heated. The sample may be known to contain the nucleic acid target for the thermal cycling reaction, or may be a test sample (wherein it is not known whether the nucleic acid target is present). In some embodiments, the sample may be derived from a cell or tissue culture. The nucleic acid target may be a HCV sequence. The sample may be derived from a patient. The method of the invention may be used to diagnose HCV infection in a patient.

Anticoagulant

The present invention also relates to an anticoagulant for use in any of the methods of the invention. In one embodiment the anticoagulant comprises arginine and $MgCl_2$ and/or Tris (pH 8.5). The Tris preferably comprises Tris (pH 8.5). The arginine may be L-arginine, D-arginine or a mixture of D- and L-arginine. The anticoagulant may be provided in a solution with reagents suitable for performing a thermal cycling reaction.

Reaction Mix

The inventors have developed a mixture of reagents that prevent the coagulation of plasma or serum proteins upon heating to 95° C., therefore allowing the direct input into the PCR. The invention can be used as an up-front plasma/serum preparation step for any blood borne diagnostic method. In one embodiment, the present invention relates to a reaction mix comprising the anticoagulant of the invention comprising 5 mg/ml L-arginine, 50 mM Tris and 5 mM $MgCl_2$. The arginine may be L-arginine, D-arginine or a mixture of D- and L-arginine.

Kit

The present invention also relates to a kit comprising a sample tube; reagents necessary and sufficient to perform a thermal cycling reaction; and arginine. Preferably the arginine is provided in the sample tube. The arginine may be L-arginine, D-arginine or a mixture of D- and L-arginine. Preferably, the reagents of the kit are provided in a lyophilised form. In one embodiment the reagents comprise $MgCl_2$ and/or Tris, preferably Tris (pH 8.5). The kit may also include instructions for use with the kit.

The sample tube may form part of a reaction vessel assembly as described in WO/2012/059751[52], comprising at least one reaction vessel having a mouth, a body, and a tip; and a casing defining a cavity having an opening, the casing further having an engaging surface; wherein in a first configuration the reaction vessel is received within the cavity of the casing via the opening, and in a second configuration the engaging surface of the casing engages with the mouth of the reaction vessel to close the mouth.

In another embodiment of the invention, the thermal cycling reaction for which the reagents are necessary and sufficient is PCR. The kit may also comprise a protease, for example Protease K or Protease. The protease is preferably suitable for digesting a viral capsid, most preferably the HCV capsid, in order to release viral genetic material. The protease is preferably a serine protease isolated from a *Bacillus* strain. The protease is preferably provided in the sample tube and or provided in a lyophilised form.

EXAMPLES 1.1. Introduction

The invention was initially developed for use in conjunction with the Genedrive Hepatitis C Kit. The Genedrive Hepatitis C Assay requires the use of a proteolytic enzyme (Protease) to aid in the release of the RNA target by digestion of the viral particles. Temperatures of 95° C. are required for the denaturation of the enzyme prior to the reverse transcription phase of PCR.

Consequently, without the presence of any preventative reagents plasma protein thermal coagulation occurs. In order to avoid introducing additional processing steps, it was investigated whether an anti-aggregation agent could prevent coagulation of the samples at concentrations insufficient to inhibit a subsequent thermal cycling reaction.

1.2. Materials and Methods 1.2.1. Protease Digestion in the Presence of Arginine Plasma samples were initially diluted 1:3 in water prior to proteolytic digestion with 2 mg/ml of Protease (Qiagen; product number 19157). The protease is a serine protease isolated from a recombinant *Bacillus* strain. The samples were incubated at 37° C. for 15 minutes and then heated to 95° C. for 5 minutes. The samples were then pelleted to visualise the coagulation effects. To assess the effects of arginine on thermal coagulation, the samples were supplemented with arginine variants, L-, D- and a mixture of L- and D-(DL) with a final working concentration of 10 mg/ml.

The controls consisted of digested plasma with water only or with PCR reagents (Ready To Go beads, GE Healthcare) to mimic standard PCR conditions.

1.2.2. PCR Tolerance of Arginine

Details of the HCV Genedrive PCR assay have been previously described[53]. The PCR was performed in the presence of L-arginine at a final concentration of 5 mg/ml (28.7 mM), 2.5 mg/ml (14.4 mM), 1.25 mg/ml (7.18 mM), and 0.625 mg/ml (3.58 mM). Two replicates were performed for each concentration, per PCR run. A water only control was also included.

1.2.3. Minimal Arginine Concentration Required in Combination with $MgCl_2$ and Tris (pH8.5)

The plasma was pre-diluted 1:3 in water, supplemented with 2 mg/ml Protease, 2.5 mM $MgCl_2$, and 12.5 mM Tris (pH8.5), together with varying concentrations of L-arginine: 5 mg/ml (28.7 mM), 2.5 mg/ml (14.4 mM), 1.25 mg/ml (7.18 mM), and 0.625 mg/ml (3.58 mM). The plasma was incubated for 10 minutes at 37° C., followed by denaturation at 95° C. for 10 minutes, then pelleted to visualise the coagulation effects.

1.2.4. The Effect of Anticoagulation Agents on Plasma and Serum Samples

Plasma and serum samples were tested either neat, or diluted 1:2, or 1:3 in water prior to supplementation with and without the anticoagulant. All samples were Protease treated (2 mg/ml), incubated at 37° C. for 10 minutes, and denatured at 95° C. for 10 minutes, then pelleted to visualise the coagulation effects.

1.3. Results 1.3.1. Arginine Prevents the Coagulation of Plasma Proteins

Figure 1B:
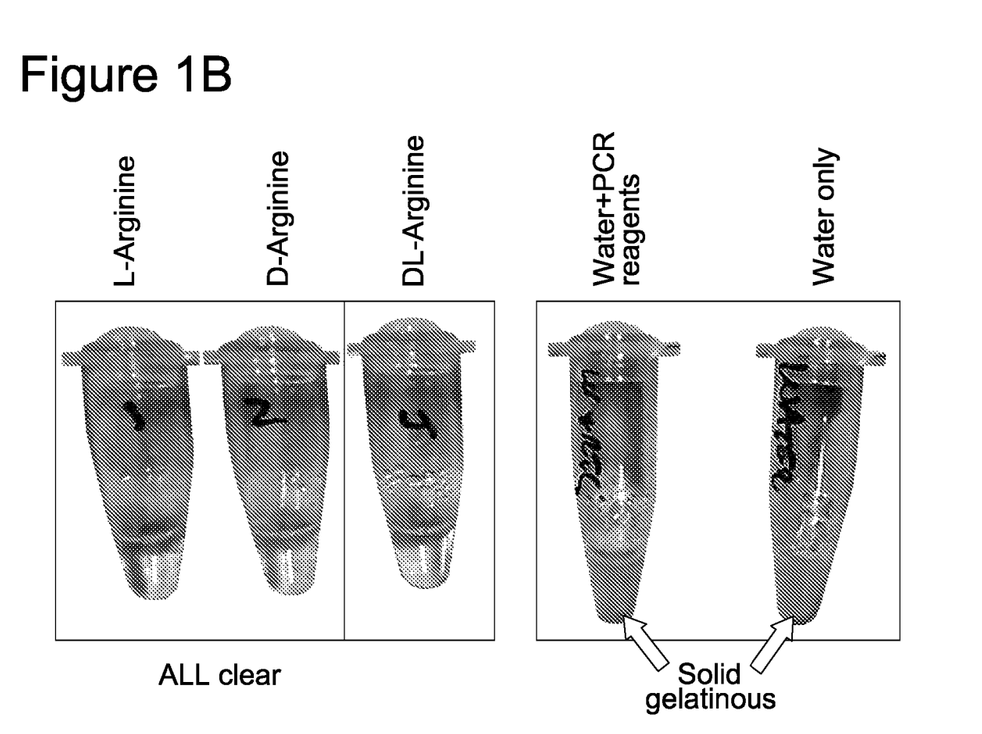

The effect of arginine on the coagulation of plasma was assessed. Plasma samples heated to 95° C. following proteolytic digestions did not coagulate when heated in the presence of any of the arginine chimeric variants (L-, D- and a mixture of L- and D-(DL)). The control samples formed a solid gelatinous mass (FIG. 1B). These data demonstrated that all of the arginine variants prevent thermal coagulation of plasma proteins.

1.3.2. PCR Tolerance to Arginine

Figure 2:
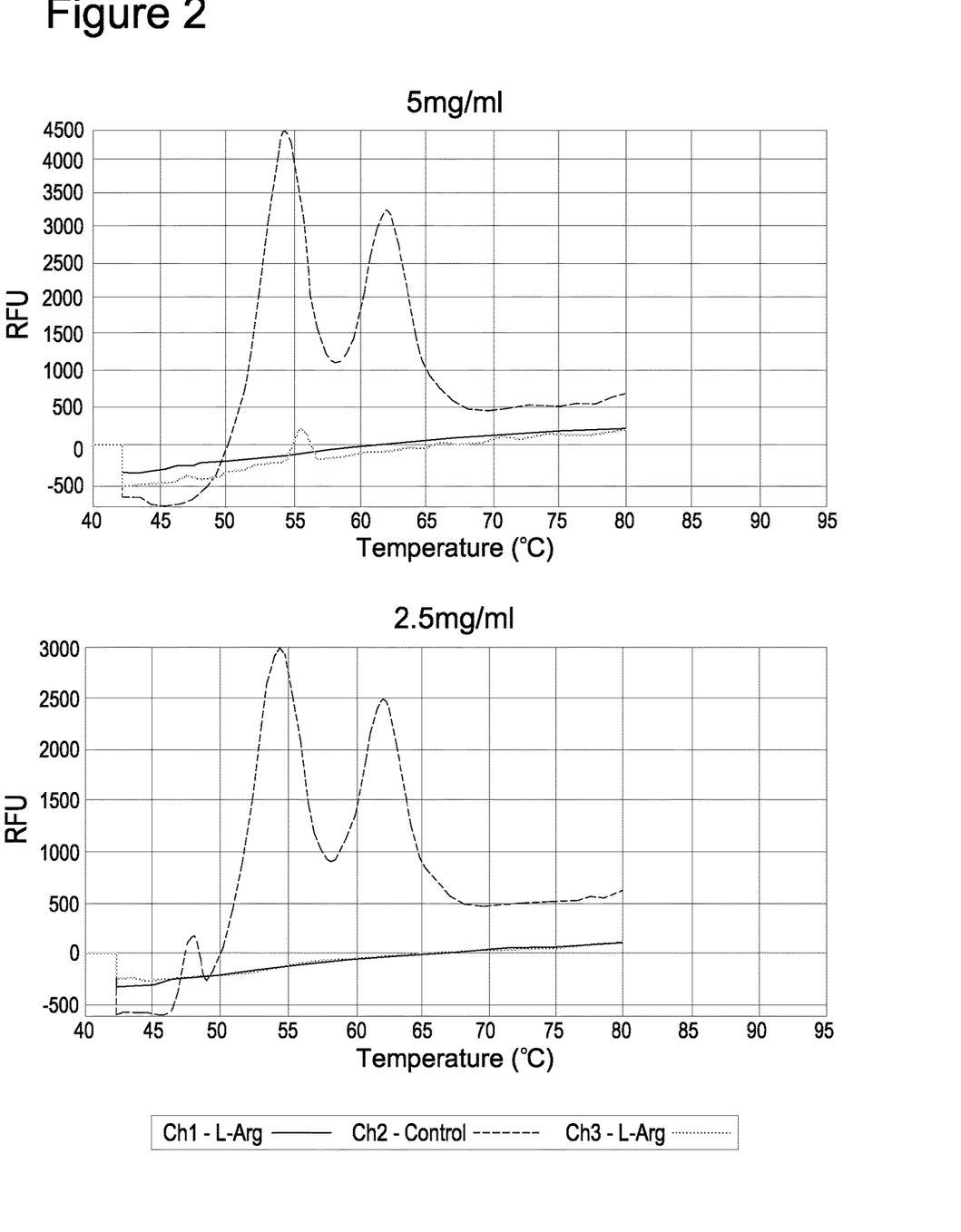
FIG. 2. Tolerance of PCR to L-arginine
The effect of different L-arginine concentrations on PCR. Two replicates were performed for each concentration per PCR run and a water only control was also included.
Figure 3:
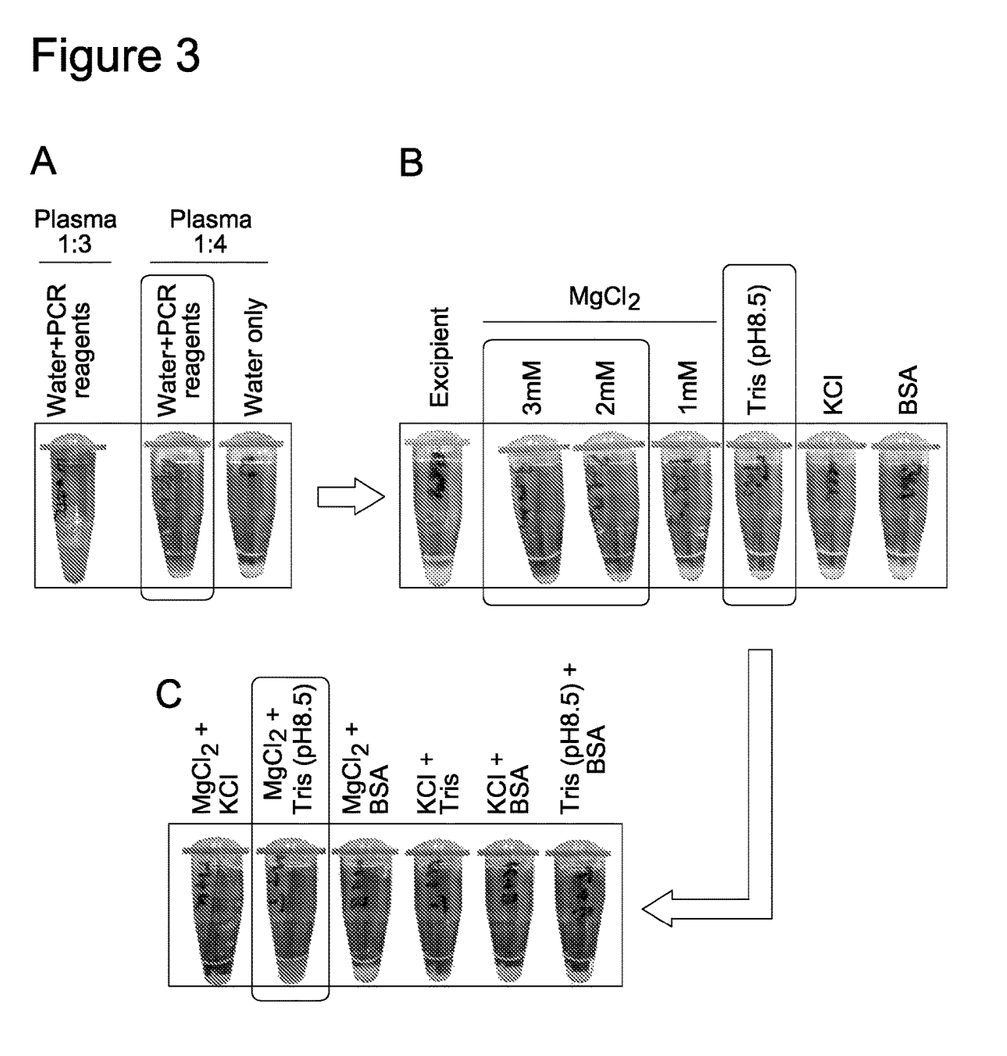
FIG. 3. The effects of PCR component on plasma coagulation
A: The effect of PCR reagents on coagulation of plasma diluted 1:3 or 1:4. B: The effect of $MgCl_2$ (1-3 mM), KCl, Tris (pH 8.5) and BSA on plasma coagulation. C: The effect of different combinations of PCR reagents on plasma coagulation: $MgCl_2$+KCl; $MgCl_2$+Tris (pH 8.5); $MgCl_2$+BSA; KCl+Tris, KCl+BSA, Tris (pH 8.5)+BSA.

To identify the tolerance levels of L-arginine on PCR, a model Genedrive® assay was subjected to supplementation with differing concentrations of L-arginine. The PCR was shown to tolerate L-arginine concentrations of at least 1.25 mg/ml (FIG. 2). Surprisingly, it was observed that the PCR reagent (arginine negative) control sample also had reduced coagulation compared to the water only sample (FIG. 3A). This effect was only observed when the plasma sample was diluted 1:4.

1.3.3. $MgCl_2$ and Tris (pH 8.5) Prevent the Coagulation of Plasma Proteins

The individual PCR components of the PCR reagent sample responsible for preventing coagulation were identified as $MgCl_2$ and Tris (pH 8.5) (FIG. 3B). A 2 mM concentration of $MgCl_2$ was sufficient to prevent thermal coagulation. KCl and BSA in isolation did not prevent thermal coagulation. The anti-coagulation effect of $MgCl_2$ and Tris (pH 8.5) was synergistic (FIG. 3C).

Figure 4:
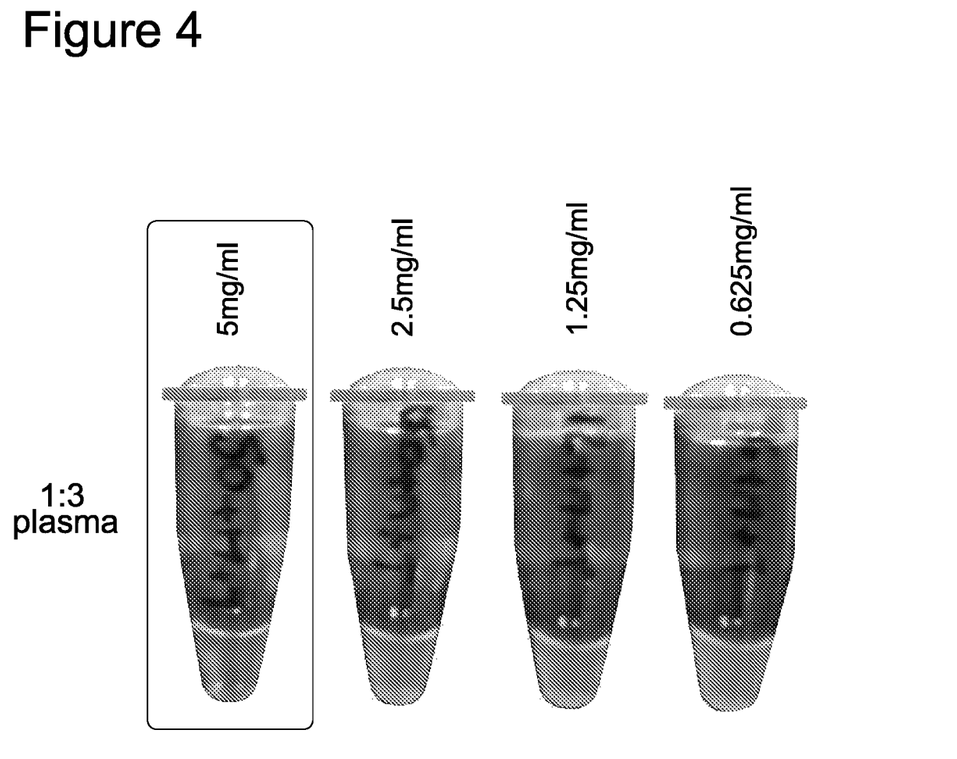

1.3.4. $MgCl_2$ and Tris (pH 8.5) Prevent the Coagulation of Plasma and Serum Proteins The minimal L-arginine concentration required to prevent thermal induced plasma protein coagulation in a sample containing $MgCl_2$ and Tris (pH8.5) reagents was investigated. The highest concentration of L-arginine (5 mg/ml) tested had the greatest effect on preventing plasma protein coagulation (FIG. 4). During a standard PCR workflow, the protease treated plasma is further diluted 3 fold with the RT-PCR reagents. An initial L-arginine concentration of 5 mg/ml in the plasma is thus diluted to a final working concentration of 1.7 mg/ml. This concentration is tolerated by a PCR (FIG. 2). The working concentrations of $MgCl_2$ and Tris (pH 8.5) required to prevent thermal induced protein were optimized, and are represented in Table 2.

TABLE 2

| Final Reagent Formulation | | |
|---|---|---|
| Procedure | Reagent | Working Concentration |
| Viral particle and plasma/serum protein digestion | Protease | 2 mg/ml |
| Anti-thermal coagulation reagents | L-Arginine | 5 mg/ml |
| | $MgCl_2$ | 5 mM |
| | Tris (pH8.5) | 50 mM |

Figure 5:
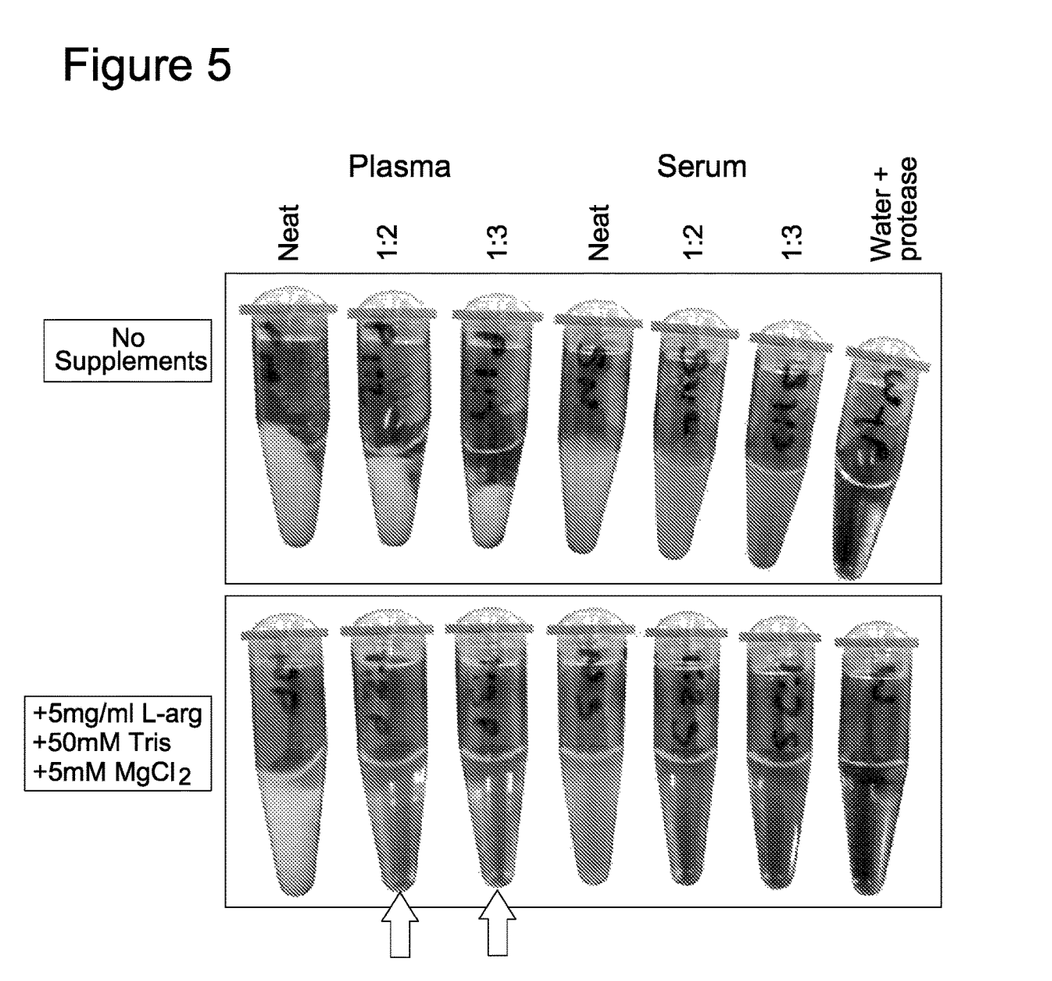

The optimized formulation of anti-thermal coagulation formulation was also shown to prevent thermal coagulation of serum samples (FIG. 5).

REFERENCES

1. Ballou, G., Luck, J. & Lum, F. The Heat Coagulation of Human Serum Albumin. *J. Biol. Chem.* 153, 589-605 (1944).
2. Huggins, C. & Jensen, E. V. Thermal coagulation of serum proteins; the effects of iodoacetate, iodoacetamide, and thiol compounds on coagulation. *J. Biol. Chem.* 179, 645-654 (1949).
3. Goldenberger, D., Perschil, I., Ritzler, M. & Altwegg, M. A simple 'universal' DNA extraction procedure using SDS and proteinase K is compatible with direct PCR amplification. *PCR Methods Appl.* 4, 368-370 (1995).
4. Hamada, H., Arakawa, T. & Shiraki, K. Effect of additives on protein aggregation. *Curr. Pharm. Biotechnol.* 10, 400-407 (2009).
5. Eva, C. Excipients and their Effects on the Quality of Biologics. (2012).
6. Reddy K, R. C., Lilie, H., Rudolph, R. & Lange, C. L-Arginine increases the solubility of unfolded species of hen egg white lysozyme. *Protein Sci. Publ. Protein Soc.* 14, 929-935 (2005).
7. Kerwin, B. A., Heller, M. C., Levin, S. H. & Randolph, T. W. Effects of Tween 80 and sucrose on acute short-term stability and long-term storage at −20 degrees C. of a recombinant hemoglobin. *J. Pharm. Sci.* 87, 1062-1068 (1998).
8. Kreilgaard, L. et al. Effect of Tween 20 on freeze-thawing- and agitation-induced aggregation of recombinant human factor XIII. *J. Pharm. Sci.* 87, 1597-1603 (1998).
9. Zoueva, O. P., Bailly, J. E., Nicholls, R. & Brown, E. G. Aggregation of influenza virus ribonucleocapsids at low pH. *Virus Res.* 85, 141-149 (2002).
10. Edwin, F., Sharma, Y. V. & Jagannadham, M. V. Stabilization of molten globule state of papain by urea. *Biochem. Biophys. Res. Commun.* 290, 1441-1446 (2002).
11. Arakawa, T. & Timasheff, S. N. Stabilization of protein structure by sugars. *Biochemistry* (Mosc.) 21, 6536-6544 (1982).
12. Neagu, A., Neagu, M. & Der, A. Fluctuations and the Hofmeister effect. *Biophys. J.* 81, 1285-1294 (2001).

13. Se, B. & A, B. Detection and prevention of protein aggregation before, during, and after purification. *Anal. Biochem.* 316, 223-231 (2003).
14. Lange, C. & Rudolph, R. Suppression of protein aggregation by L-arginine. *Curr. Pharm. Biotechnol.* 10, 408-414 (2009).
15. Schrader, C., Schielke, A., Ellerbroek, L. & Johne, R. PCR inhibitors—occurrence, properties and removal. *J. Appl. Microbiol.* 113, 1014-1026 (2012).
16. Bickley, J., Short, J. K., McDowell, D. G. & Parkes, H. C. Polymerase chain reaction (PCR) detection of *Listeria monocytogenes* in diluted milk and reversal of PCR inhibition caused by calcium ions. *Lett. Appl. Microbiol.* 22, 153-158 (1996).
17. Al-Soud, W. A. & Rådström, P. Purification and characterization of PCR-inhibitory components in blood cells. *J. Clin. Microbiol.* 39, 485-493 (2001).
18. Wilson, I. G. Inhibition and facilitation of nucleic acid amplification. *Appl. Environ. Microbiol.* 63, 3741-3751 (1997).
19. Geng, T. & Mathies, R. A. Minimizing inhibition of PCR-STR typing using digital agarose droplet microfluidics. *Forensic Sci. Int. Genet.* 14, 203-209 (2015).
20. Rossen, L., Nørskov, P., Holmstrøm, K. & Rasmussen, O. F. Inhibition of PCR by components of food samples, microbial diagnostic assays and DNA-extraction solutions. *Int. J. Food Microbiol.* 17, 37-45 (1992).
21. Katcher, H. L. & Schwartz, I. A distinctive property of Tth DNA polymerase: enzymatic amplification in the presence of phenol. *BioTechniques* 16, 84-92 (1994).
22. Ahokas, H. & Erkkilä, M. J. Interference of PCR amplification by the polyamines, spermine and spermidine. *PCR Methods Appl.* 3, 65-68 (1993).
23. Monteiro, L. et al. Complex polysaccharides as PCR inhibitors in feces: *Helicobacter pylori* model. *J. Clin. Microbiol.* 35, 995-998 (1997).
24. Wei, T., Lu, G. & Clover, G. Novel approaches to mitigate primer interaction and eliminate inhibitors in multiplex PCR, demonstrated using an assay for detection of three strawberry viruses. *J. Virol. Methods* 151, 132-139 (2008).
25. Ijzerman, M. M., Dahling, D. R. & Fout, G. S. A method to remove environmental inhibitors prior to the detection of waterborne enteric viruses by reverse transcription-polymerase chain reaction. *J. Virol. Methods* 63, 145-153 (1997).
26. Belec, L. et al. Myoglobin as a polymerase chain reaction (PCR) inhibitor: A limitation for PCR from skeletal muscle tissue avoided by the use of *Thermus thermophilus* polymerase. *Muscle Nerve* 21, 1064-1067 (1998).
27. Akane, A., Matsubara, K., Nakamura, H., Takahashi, S. & Kimura, K. Identification of the Heme Compound Copurified with Deoxyribonucleic Acid (DNA) from Bloodstains, a Major Inhibitor of Polymerase Chain Reaction (PCR) Amplification. *J. Forensic Sci.* 39, 362-372 (1994).
28. Al-Soud, W. A., Jönsson, L. J. & Rådström, P. Identification and characterization of immunoglobulin G in blood as a major inhibitor of diagnostic PCR. *J. Clin. Microbiol.* 38, 345-350 (2000).
29. Holodniy, M. et al. Inhibition of human immunodeficiency virus gene amplification by heparin. *J. Clin. Microbiol.* 29, 676-679 (1991).
30. Izraeli, S., Pfleiderer, C. & Lion, T. Detection of gene expression by PCR amplification of RNA derived from frozen heparinized whole blood. *Nucleic Acids Res.* 19, 6051 (1991).
31. Fredricks, D. N. & Relman, D. A. Improved amplification of microbial DNA from blood cultures by removal of the PCR inhibitor sodium polyanetholesulfonate. *J. Clin. Microbiol.* 36, 2810-2816 (1998).
32. Friedland, L. R., Menon, A. G., Reising, S. F., Ruddy, R. M. & Hassett, D. J. Development of a polymerase chain reaction assay to detect the presence of *Streptococcus pneumoniae* DNA. *Diagn. Microbiol. Infect. Dis.* 20, 187-193 (1994).
33. Garcia, M. E., Blanco, J. L., Caballero, J. & Gargallo-Viola, D. Anticoagulants interfere with PCR used to diagnose invasive aspergillosis. *J. Clin. Microbiol.* 40, 1567-1568 (2002).
34. Abbaszadegan, M., Huber, M. S., Gerba, C. P. & Pepper, I. L. Detection of enteroviruses in groundwater with the polymerase chain reaction. *Appl. Environ. Microbiol.* 59, 1318-1324 (1993).
35. Burkardt, H. J. Standardization and quality control of PCR analyses. *Clin. Chem. Lab. Med.* 38, 87-91 (2000).
36. John, M. E. An efficient method for isolation of RNA and DNA from plants containing polyphenolics. *Nucleic Acids Res.* 20, 2381 (1992).
37. Opel, K. L., Chung, D. & McCord, B. R. A study of PCR inhibition mechanisms using real time PCR. *J. Forensic Sci.* 55, 25-33 (2010).
38. Saulnier, P. & Andremont, A. Detection of genes in feces by booster polymerase chain reaction. *J. Clin. Microbiol.* 30, 2080-2083 (1992).
39. Wiedbrauk, D. L., Werner, J. C. & Drevon, A. M. Inhibition of PCR by aqueous and vitreous fluids. *J. Clin. Microbiol.* 33, 2643-2646 (1995).
40. Demeke, T. & Jenkins, G. R. Influence of DNA extraction methods, PCR inhibitors and quantification methods on real-time PCR assay of biotechnology-derived traits. *Anal. Bioanal. Chem.* 396, 1977-1990 (2010).
41. Widjojoatmodjo, M. N., Fluit, A. C., Torensma, R., Verdonk, G. P. & Verhoef, J. The 50 magnetic immuno polymerase chain reaction assay for direct detection of salmonellae in fecal samples. *J. Clin. Microbiol.* 30, 3195-3199 (1992).
42. Boye, J. in *Food Proteins and Their Applications* (CRC Press, 1997).
43. Ochman, H. Inverse Polymerase Chain Reaction. *Nat. Biotechnol.* 8, 759-760 (1990).
44. Troutt, A. B., McHeyzer-Williams, M. G., Pulendran, B. & Nossal, G. J. Ligation-anchored PCR: a simple amplification technique with single-sided specificity. *Proc. Natl. Acad. Sci. U.S.A.* 89, 9823-9825 (1992).
45. William, H. The essential prerequisites for quantitative RT-PCR. *Nat. Biotechnol.* 17, (1999).
46. Vincent, M., Xu, Y. & Kong, H. Helicase-dependent isothermal DNA amplification. *EMBO Rep.* 5, 795-800 (2004).
47. Yeku, O. & Frohman, M. A. Rapid amplification of cDNA ends (RACE). *Methods Mol. Biol.* Clifton N.J. 703, 107-122 (2011).
48. Narhi, L. O., Schmit, J., Bechtold-Peters, K. & Sharma, D. Classification of protein aggregates. *J. Pharm. Sci.* 101, 493-498 (2012).
49. Das, U. et al. Inhibition of protein aggregation: supramolecular assemblies of arginine hold the key. *PloS One* 2, e1 176 (2007).
50. Cobb, B. Thermal Cycler. (2012).

51. Cobb, B. Method and system for thermocycling. (2012).
52. Cobb, B. Reaction Vessel. (2012).
53. Albert, M. PoC HCV Final Report. (2016).

What is claimed is:

1. A method of performing a thermal cycling reaction comprising:
   a. mixing a sample comprising blood, serum, or plasma with i) an anticoagulant comprising arginine and ii) reagents necessary and sufficient for performing a PCR thermal cycling reaction in the sample in the presence of a target nucleic acid, and
   b. incubating the sample under thermal cycling conditions, wherein the anticoagulant protects the PCR thermal cycling reaction from inhibition by coagulated proteins in the sample.

2. The method of claim 1, wherein the sample is diluted by less than a factor of 10 prior to the thermal cycling reaction.

3. The method of claim 1, wherein the sample is mixed with arginine to give an arginine concentration of 2-6 mg/ml.

4. The method of claim 3, further comprising the step of diluting the sample, wherein the sample is diluted following mixing with arginine and prior to incubating the sample under thermal cycling conditions.

5. The method of claim 4, wherein the concentration of arginine in the sample during incubation of the sample under thermal cycling conditions is 0.5-2 mg/ml.

6. The method of claim 1, wherein the reagents and anticoagulant are provided in a single solution.

7. The method of claim 1, wherein the anticoagulant comprises $MgCl_2$.

8. The method of claim 7, wherein the sample is mixed with $MgCl_2$ to give a $MgCl_2$ concentration of 2-6 mM.

9. The method of claim 1, wherein the anticoagulant comprises Tris.

10. The method of claim 9, wherein the sample is mixed with Tris to give a Tris concentration of 30-60 mM.

11. The method of claim 1 further comprising the step of adding protease to the sample prior to incubating the sample under thermal cycling conditions.

12. The method of claim 1, wherein the sample is subjected to protein denaturing conditions prior to incubating the sample under thermal cycling conditions.

13. The method of claim 1, wherein the sample comprises serum or plasma.

14. The method of claim 13, wherein the sample comprises diluted serum or plasma.

15. The method of claim 14, wherein the serum or plasma is diluted in water.

* * * * *